(12) United States Patent
Andreiko (10) Patent No.: US 7,094,053 B2
(45) Date of Patent: Aug. 22, 2006

(54) CUSTOM JIG FOR PLACING ORTHODONTIC BRACKETS AND METHODS OF MAKING AND USING SAME

(75) Inventor: Craig A. Andreiko, Alta Loma, CA (US)

(73) Assignee: Ormco Corporation, Orange, CA (US)

( * ) Notice: Subject to any disclaimer, the term of this patent is extended or adjusted under 35 U.S.C. 154(b) by 335 days.

(21) Appl. No.: 10/156,162

(22) Filed: May 28, 2002

(65) Prior Publication Data

US 2003/0224310 A1    Dec. 4, 2003

(51) Int. Cl.
*A61C 7/00* (2006.01)
(52) U.S. Cl. ............................................. 433/24; 433/3
(58) Field of Classification Search ................... 433/2, 433/3, 4, 24, 159
See application file for complete search history.

(56) References Cited

U.S. PATENT DOCUMENTS

| | | | |
|---|---|---|---|
| 4,183,141 A * | 1/1980 | Dellinger et al. | 433/3 |
| 4,360,341 A * | 11/1982 | Dellinger | 433/24 |
| 5,055,038 A | 10/1991 | Ronay et al. | |
| 5,114,339 A * | 5/1992 | Guis | 433/24 |
| 5,368,478 A | 11/1994 | Andreiko et al. | 433/24 |
| 5,542,842 A | 8/1996 | Andreiko et al. | 433/24 |
| 5,586,881 A * | 12/1996 | Chikami | 433/3 |
| 5,791,896 A * | 8/1998 | Ipenburg | 433/3 |
| 5,863,198 A * | 1/1999 | Doyle | 433/3 |
| 6,123,544 A | 9/2000 | Cleary | |
| 6,193,514 B1 * | 2/2001 | Horan | 433/141 |
| 6,554,613 B1 * | 4/2003 | Sachdeva et al. | 433/24 |
| 2001/0018175 A1 | 8/2001 | Kim | |
| 2002/0025503 A1 | 2/2002 | Chapoulaud et al. | |

FOREIGN PATENT DOCUMENTS

| | | |
|---|---|---|
| JP | 2002 102256 A | 4/2002 |
| WO | WO 01/47405 | 7/2001 |

* cited by examiner

*Primary Examiner*—Cary E. O'Connor
(74) *Attorney, Agent, or Firm*—Wood, Herron & Evans, L.L.P.

(57) ABSTRACT

A placement jig for locating an orthodontic appliance on a tooth is provided with a cavity formed in a jig body and conforming to the contour of an occlusal portion a tooth crown, which cavity is coated with a releasable adhesive to hold the jig to the tooth as the appliance is bonded to the tooth. Connecting structure is fixed to the jig body and has a spring metal tip that frictionally fits into a hole in the appliance. The peg is oriented in the occlusal-gingival direction so that its tip slides out of the hole in the bracket when the jig is moved occlusally from the tooth to remove the jig after the appliance has been bonded. A handle is formed into or extends from the jig body at a generally balanced position opposite the cavity, and a specially configured handling tool is provided to grip the jig and appliance combination to place it on a tooth or to remove the jig from the appliance and the tooth. The peg may be formed by from a strip of spring metal in one layer or folded with a bowed portion that is spring biased to expand and removably fit snugly in a hole in the appliance with its other end securely fixed to the jig body. For featureless teeth, registration structure can be added to the tooth or the jig can be fashioned with removeable extensions to register with an adjacent tooth.

49 Claims, 6 Drawing Sheets

CUSTOM JIG FOR PLACING ORTHODONTIC BRACKETS AND METHODS OF MAKING AND USING SAME

This application is related to U.S. patent application Ser. No. 09/941,151, filed Aug. 28, 2001, and International patent application No. PCT/US00/35558, filed Dec. 29, 2000, and U.S. Provisional Patent Application Ser. No. 60/173,890, filed Dec. 29, 1999, all of which are hereby expressly incorporated herein by reference in their entirety.

FIELD OF THE INVENTION

This invention relates to the positioning of orthodontic appliances on teeth and, more particularly, to appliance positioning jigs and to the manufacture and use of such jigs, especially custom jigs for the positioning of orthodontic appliances.

BACKGROUND OF THE INVENTION

Orthodontic appliances to position the teeth of patients are designed to contact the teeth of a patient and apply forces to those teeth that will cause the teeth to move toward an arrangement that the orthodontist determines to be ideal or to otherwise satisfy a treatment objective. Goals of orthodontic treatment include moving the teeth of a patient as closely as possible to the finish tooth positions determined ideal for achieving the desired treatment result, minimizing the time during which the patient must wear the appliances used for the treatment, and minimizing the time of the orthodontic practitioners, or chair-time, in treating the patients. All of these goals are served by reducing the amount of manual adjustment of the appliances, such as wire bending, needed by the orthodontic practitioner, during the course of the treatment of a patient with an appliance.

A most common and useful type of orthodontic appliance includes a set of brackets bonded to each of the respective teeth of a patient that support and are interconnected by a resilient archwire. The archwire is elastically deformed from its unstressed shape and applies forces to the teeth through the brackets as the wire tends to return to its unstressed shape. The trend in appliance design or selection is to employ an archwire having a predetermined shape that, when mounted on brackets secured to the teeth at predetermined design positions, will urge those teeth toward desired treatment positions without, or with minimal, intervention by the orthodontist in bending the wire. Standard appliances that are designed to anatomical averages typically require some adjustment during the course of a patient's treatment. Custom appliances ideally eliminate or minimize this need for adjustment. For the goals of minimal or no archwire adjustment to be met, however, brackets must be accurately placed on the patient's teeth at exact positions for which the appliance was designed.

For accurate placement of orthodontic brackets onto the teeth of a patient, the use of custom placement jigs has been proposed. Such jigs have been described, for example, in U.S. Pat. No. 5,368,478 and International Patent Application No. PCT/US00/35558, hereby incorporated herein by reference, to place brackets of orthodontic appliances. Such jigs may include a precision formed custom surface that is manufactured from tooth crown-shape data that has been scanned from the patient's teeth. Each such surface is intended to precisely fit over the crown of a patient's respective tooth and to hold a bracket of an orthodontic appliance against its proper design position on the tooth while the bracket is being bonded to the tooth surface.

While the provision of such jigs has gone far to serve the orthodontic objectives discussed above, there remains a need to improve the function and handling of such jigs to better serve these orthodontic objectives.

SUMMARY OF THE INVENTION

A primary objective of the present invention is to provide jigs for positioning orthodontic appliances on teeth, and particularly, jigs that can easily, efficiently and reliably be used by orthodontic practitioners to place appliances for bonding to the teeth of a patient. A particular objective of the invention is to provide an orthodontic appliance and jig combination that can be easily and accurately placed on the tooth of a patient by an orthodontic practitioner, is easily maintained on the tooth while the appliance is being bonded, can be easily separated to leave the appliance on the tooth while the jig is removed from the patient's mouth, and can be reused in the event the appliance has to be rebonded or otherwise repositioned on the tooth during patient treatment.

Another objective of the invention is to provide an efficient method of making and using appliance positioning jigs.

According to principles of the present invention, an orthodontic appliance positioning jig is provided having a jig locating surface that conforms to at least a portion of the crown of at least one tooth of the individual patient being treated. The jig is provided with an appliance connecting feature to removably hold the jig to the appliance for which the jig is designed to bond the appliance to the tooth. The jig is also provided with a crown connecting feature to removably hold the jig and appliance combination to a tooth.

According to certain embodiments of the invention, an appliance positioning jig is further provided with handle and gripping features that facilitate the handling of the jig alone, or the jig and appliance combination, to improve the efficiency of the appliance placement procedure and the accuracy of the placement of the appliance. The features, alone or in various combinations, help serve this purpose. The processes of making the jig having features of the invention and of using the jig and the features of the invention are also provided.

According, principles of the invention are provided in certain embodiments illustrated and described herein. These include providing a jig-locating surface coated with a releasable adhesive, such as a pressure sensitive or other tacky adhesive for example, that temporarily holds the jig to the tooth while the jig holds an orthodontic appliance that is connected to the jig in a position on the tooth for bonding. The releasable adhesive keeps the appliance in place while the appliance is being bonded to the tooth with an orthodontic or other dental adhesive, without relying on the practitioner to manually hold the jig during the time that the dental adhesive is setting or being cured.

According to other principles of the invention, the jig is provided with handle structure projecting from, formed on or shaped into, the jig that facilitates the holding and orienting of the appliance by a pair of tweezers, an orthodontic hand tool or other dental appliance handling device so that the appliance can be quickly and accurately positioned on the tooth of the patient and so that the jig can be easily removed from the tooth and disconnected from the bonded appliance. The handle structure is configured and located on the jig so that the combination is balanced when held thereby and so that the forces applied among the jig, the appliance and the tooth can be controlled in a balanced manner. Cooperating structure may also be provided on the handling tool to better grip the handle. The handle and tool features facilitate the placement of the jig and appliance combination on the tooth, the removal of the jig body from the surface of the tooth and the disconnecting of the jig from the appliance.

According to still other principles of the invention, structure is used to connect the orthodontic appliance in a manner that holds the appliance and jig together but permits easy removal of the jig from the appliance once the appliance is positioned and bonded on the tooth. In the described embodiment, this structure includes a peg that is fixed to the body of the jig. The peg is configured to easily separate from cooperating structure on the appliance when the jig is moved away from the crown of the tooth and the appliance is bonded to the tooth. Where the releasable adhesive is used to temporarily hold the jig to the crown of the tooth, similarly directed force, preferably applied through the handle mentioned above, removes both the jig body from the crown of the tooth and the peg of the jig from the appliance. Where handle structure is provided on the jig, such structure is configured and located so that force is applied to the jig to separate the jig locating surface from the tooth and to also separate the jig from the appliance, and to do so in a balanced and stable manner.

In one described embodiment of the invention, a custom placement jig is provided with a rigid foam body having a custom crown-conforming cavity that has been formed therein by a computerized three-dimensional manufacturing process to conform to the precise shape of an occlusal portion of the crown of a patient's tooth. The surface of the cavity is coated with a contact adhesive, a pressure sensitive adhesive or other releasable adhesive, to hold the jig to the tooth as the appliance is being bonded to the tooth.

According to additional features of the invention, structure beyond the natural features of a single tooth is provided to facilitate the unique positioning of the jig onto the crown of that tooth, which is useful in situations where the tooth crown has too few features to reliably register the jig on the tooth. According to one embodiment, registration structure is a surface variation formed on the crown of the patient's tooth, such as by the bonding of a small projection or by cutting a notch. According to another embodiment, the jig is configured to register with adjacent teeth.

With registration structure bonded to the patent's tooth, such registration structure may be placed on the tooth before an impression or scan of the crown of the tooth is made for purposes of acquiring three dimensional data to make the jig. The registration structure is then preferably left bonded to the tooth in the same position until the appliance is placed on the tooth. The cavity of the jig will be made to include the registration structure in the contour of the cavity, so that when the jig is placed on the tooth, the registration structure cooperates with other surface structure of the crown of the tooth to register with the shape of the cavity of the jig. After placement of the appliance, the registration structure can be removed from the patient's tooth. Such registration structure can also take the form of a groove or other feature formed on the tooth, or a mark printed on the tooth that can interact with a sensor in the positioning of the jig.

In the embodiment in which a jig registers with adjacent teeth, the body of the jig extends beyond the tooth on which the jig is to be placed and contacts one or both adjacent teeth, with a custom three-dimensional cavity formed in the extending part of the jig body to register with a small portion of the crown of the adjacent tooth. The formation of the cavity for the adjacent tooth is carried out in the custom jig manufacturing operation from three-dimensional data that takes into account the initial maloccluded positions of the teeth, which is typically the position in which the appliance is placed on the tooth. To facilitate reuse of the jigs in the event that an appliance must be re-bonded to a tooth during treatment and after the teeth might have moved from their initial positions, the jig body may be made such that any portion of the jig body that is to contact an adjacent tooth is removable from the rest of the jig body, since the adjacent tooth is no longer a reliable reference for the jig.

Appliance connecting structure is provided on the jig body. The appliance connecting structure is configured to hold the appliance in a precise design position for bonding against the crown of the tooth when the cavity is fit on the tooth and to release the appliance and allow the jig to be easily removed from the tooth once the appliance is bonded to the tooth. The appliance connecting structure may be structure integral to the jig body or a separate piece. Integral structure may include an extension or projection that snaps into a recess in the appliance, or a resilient socket or other recess into which a portion of the appliance fits. Separate structure may include a clip that constrains the jig to the appliance or may include a peg that fits into a hole or recess in the appliance.

In the illustrated embodiment, the connecting structure is in the form of a peg, fixed to the jig body and configured to hold the appliance in a precise design position for bonding against the crown of the tooth when the cavity is fit on the tooth. The peg is configured to support the appliance but to release the appliance easily, for example, by being provided with a spring metal tip that frictionally fits into a hole in the appliance but slides out of the hole when the jig is moved occlusally from the crown of the tooth. To this end, the peg may be oriented in the occlusal-gingival direction so that its tip slides out of the hole in the bracket when the jig is moved in an occlusal direction to remove it from the tooth after the appliance that was attached to the peg has been bonded to the tooth.

A handle may be provided on the jig body at a generally balanced position opposite the cavity, and a specially configured tweezers or other opposed-jaw gripper tool, or other handling tool may be provided for the practitioner to grip the handle to carry the jig and appliance combination to place it on a tooth or to remove the jig from the appliance and the tooth.

A method for forming suitable peg connecting structure is also provided. The peg may be formed by cutting it from a strip of spring metal and folding and welding the two halves of the strip together so that its folded end is spring biased to expand to be removably inserted in a hole in the appliance while the other end of the peg is securely fixed to the jig body. The peg is preferably made of spring metal and formed by folding a strip of the metal such that the tip of the peg resiliently expands outwardly so that the peg will hold the appliance to the jig by friction when the folded tip of the peg is fit into a hole in the appliance. A precise stop is formed on the peg so that the appliance is held at a precise position relative to the cavity that is formed in the jig body. The opposite ends of the strip are folded against each other and spot welded together, and have serrated edges that lock the peg in a hole in the jig body so it will not pull out after assembly.

One suitable method by which the jig body is formed is by milling the custom tooth conforming cavity on one side thereof and precisely locating a peg mounting hole using computerized milling equipment that forms the cavity, to thereby insure that the peg mounting hole and the cavity have an intended relationship. Laser forming methods, stereo lithographic methods or other suitable forming methods may be used.

The combination of jig and appliance is achieved, for example, by providing the jig body with the peg attached and coating the cavity of the jig body with releasable adhesive. An orthodontic appliance is connected to the jig by fitting a precisely located hole therein onto the tip of the peg and sliding it onto the peg until a stop on the peg limits the sliding. Handle structure is provided on the jig body opposite the cavity to allow handling of the jig and appliance combination. Standard as well as custom orthodontic appliances may be placed with the jig.

The orthodontic practitioner preferably uses the jig by engaging the handle of the jig, with the appliance so attached, using a tweezers that is specifically configured to efficiently grip the handle. The combination is placed with the tweezers onto the crown of the one tooth of the patient for which it was designed, which causes the bonding base of the appliance to locate at its precise design position on the surface of the tooth. Prior to placement, the practitioner either applies dental adhesive to the base of the appliance or uses an appliance to which adhesive has been pre-applied by the appliance manufacturer. The dental adhesive is typically a thermosetting adhesive such as a LJV curable adhesive that will set upon exposure to ultraviolet light, or may, when being applied by the practitioner, be a multiple part adhesive. When the jig is placed on the tooth crown, it is held there by the releasable adhesive, which frees the hands of the practitioner. When the dental adhesive is cured, the appliance is securely bonded to the tooth. Then the jig can be lifted from the tooth by gripping the handle with the tweezers and moving the jig in the occlusal direction, releasing the releasable adhesive from the tooth crown and pulling the peg from the appliance.

The invention provides for the efficient and accurate placement of orthodontic appliances on the teeth of patients.

The features described herein are particularly useful for custom placement jigs that are useful in placing standard or custom orthodontic appliances. Furthermore, certain of the features described herein are also useful for placement jigs that are not customized for individual patients.

These and other objectives and advantages of the present invention will be more readily apparent from the following detailed description of the drawings, in which:

DETAILED DESCRIPTION OF THE DRAWINGS

Figure 1:
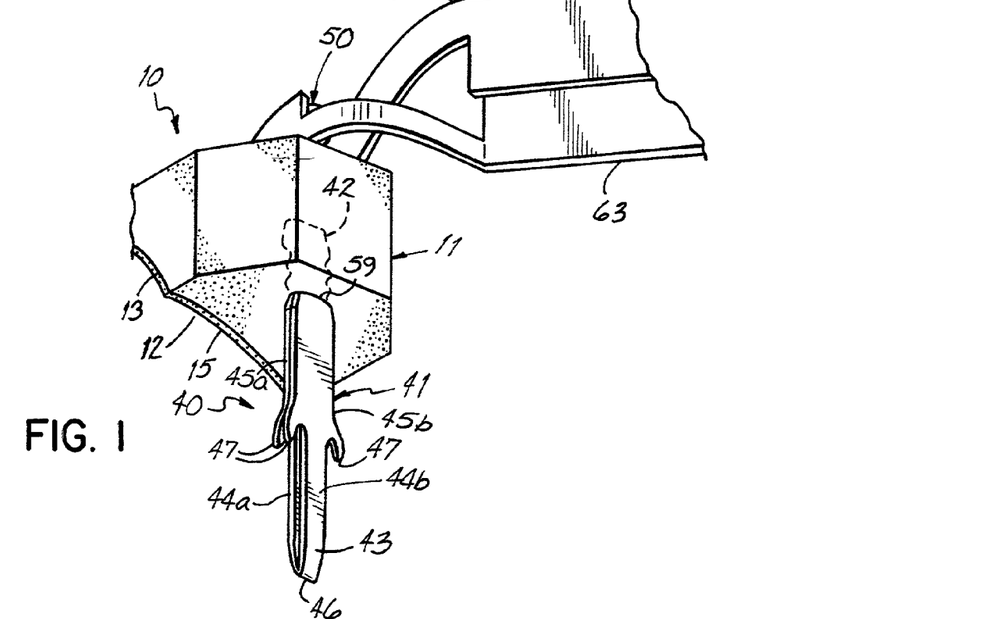
FIG. 1 is a perspective view of an orthodontic bracket placement jig according to certain embodiments of the present invention.

FIG. 1 illustrates a bracket positioning jig 10 for use in locating a custom orthodontic appliance on a patient's tooth for bonding. The jig 10 includes a jig body 11 formed of a single piece of material. A cavity, socket or concave depression 12 is machined into the jig body 11. The wall of the cavity 12 in the body 11 functions as a jig locating surface 13 that is configured to conform precisely to a unique portion of the crown of one of the teeth of a patient, preferably to a portion of the crown approximately centered on the occlusal surface of the tooth.

Figure 2:
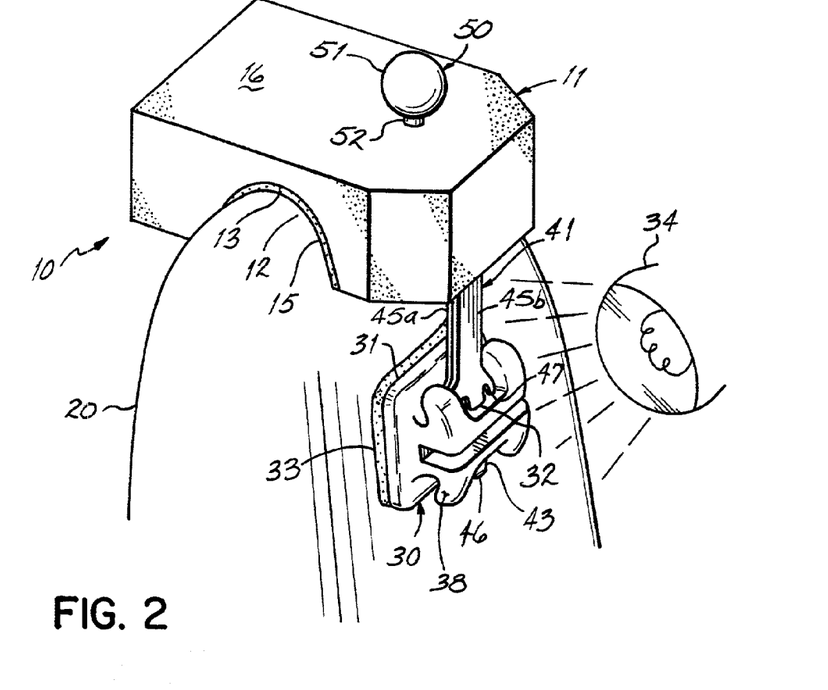
FIG. 2 is a perspective view of the jig of FIG. 1, illustrated in combination with an orthodontic bracket, and shown being placed in position on the crown of a tooth of a patient according to principles of the present invention.

In FIG. 2 the jig 10 is illustrated with the jig-locating surface 13 positioned on an area of the crown of the tooth 20 that is generally centered on the occlusal edge of a tooth 20 of a patient, which tooth 20 is illustrated as a lower central incisor of the patient. The jig 10 is shown holding an orthodontic appliance in the form of an orthodontic bracket 30, which has a bonding base or pad 31 to which extends an archwire support 38 having an archwire slot therein. The jig 10 is shown holding the bracket 30 with its bonding base 31 against the facial side of the tooth 20 in the position in which it was designed to function as part of an orthodontic appliance set that was preferably custom designed for the treatment of the specific patient. Orthodontic brackets are currently the type of appliance most often expected to be placed using jigs described herein; nonetheless, while described herein for use in positioning brackets, the jig 10 may be used to position other types of appliances or appliance securing or aligning structures on teeth. Such a bracket 30, when its base is bonded to the tooth 20 in this position, is typically interconnected by an orthodontic archwire (not shown) of the orthodontic appliance set, of which the bracket 30 is a component, to brackets similarly designed for and bonded to other teeth of the patient.

The material of which the body 11 of the jig 10 is made may be any economical rigid material that is compatible with oral orthodontic treatment and can be formed with sufficient precision and at sufficiently low cost into a placement jig capable of settling in a unique predetermined position on the crown of a patient's tooth when placed on the crown and urged against it with a minimal force applied by the hand of an orthodontic practitioner. A foam material, such as a rigid foam material or a compliant foam material, is useful. A rigid foam material, for example, such as the prototyping material sold by General Plastics Mfg. Co. of Tacoma, Wash., under the name LAST-A-FOAM, has been found suitable. This foam material can be milled with a precision computer-controlled cutting tool driven by three-dimensional data that defines the shape of the crown of the patient's tooth. Such data may be that derived, for example, by scanning systems referred to in the related applications identified above and incorporated by reference. Alternatively, the body 11 of the jig 10 may be molded and made of thermoplastic material. The mold may, in turn, be formed by computer-controlled equipment to conform to the three-dimensional crown of the patient's tooth.

According to one feature of the invention, a releasable adhesive coating 15 covers the surface 13 that lines the cavity 12. The adhesive coating 15 holds the jig 10 on the crown of the tooth 20 in the position in which it was placed by the practitioner, and holds the base 31 of the bracket 30 against the surface of the tooth in the position at which it is to be bonded so that the practitioner need not continue to hold the combination as the dental adhesive 33 being used to bond the base 31 to the tooth surface cures. The releasable adhesive may be any of several types of adhesive, such as a pressure sensitive adhesive. One acceptable adhesive that can be used for the coating 15 is an acrylic emulsion adhesive marketed under the trademarks PROS-AIDE and PROS-AIDE II by Cybergraphic Designs, Inc.

According to another feature of the invention, orthodontic appliance connecting structure 40 is fixed to the jig body 11. The appliance connecting structure 40 is configured so that it holds the appliance to the jig for transporting to the patient's tooth, but releases the appliance once it is bonded to the tooth, leaving it on the tooth, as the jig is removed from the tooth crown. In the illustrated embodiment, the appliance connecting structure 40 is in the form of a pin or peg 41 that slips into and out of a hole 32 in the bracket 30 when the jig is respectively moved occlusally and gingivally onto and off of the crown of the tooth and relative to a bracket 30 that is mounted in its design position on the crown of the tooth, typically in a vertical direction. In the orientation illustrated in FIGS. 1 and 2 with the tooth 20 being a lower tooth, the pin 41 is fixed to the jig body 11 at its proximate end 42 and has a remote end 43 that is dimensioned to form a friction fit with the sides of the hole 32 in the bracket 30. In the embodiment shown, the remote lower end 43 of the peg 41 is formed of two spring metal members 44a,44b that are spring biased to expand away from each other, as described in more detail below. The hole 32 in the bracket 30 is specially configured cooperating structure on the appliance that is designed to function with the peg end 43 to releasably carry the bracket 30 on the jig 10.

Figure 3:
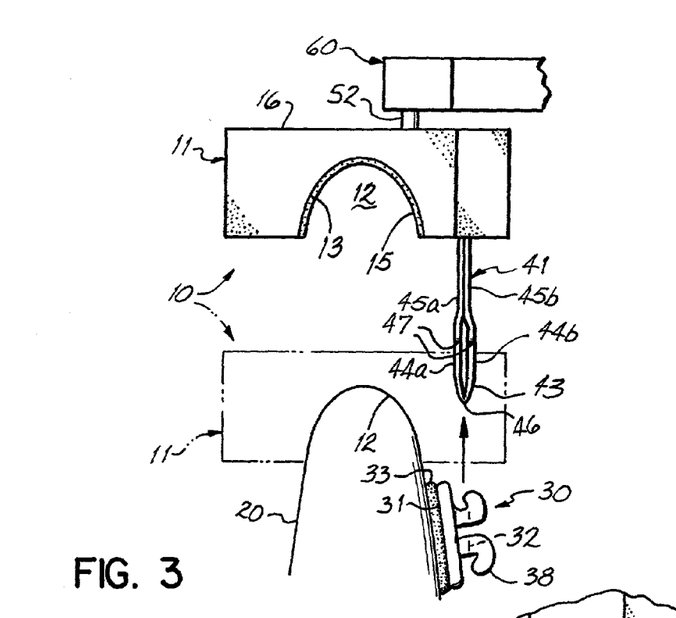
FIG. 3 is a side view illustrating the placement of an orthodontic bracket on the tooth of a patient, as shown in FIG. 2, with a placement jig according to principles of the present invention.

According to another feature of the invention, handle structure 50 is provided on the body 11 of the jig 10. The handle structure 50 is located on a surface 16 of the jig body 11 opposite the surface 12. The handle structure 50 is configured to be gripped by tweezers or some other hand tool by the orthodontic practitioner. In FIGS. 1 and 2, the handle structure 50 is illustrated as a generally spherical knob or ball 51. The knob or ball 51 has a post 52 that is fixed to and extends the ball 51 away from the surface 16 of the jig body 11. This handle structure 50 is positioned generally directly over the occlusal edge of the tooth 20 or slightly to the facial side thereof, so that downward or upward force can be applied to the handle without the jig and appliance rotating about a horizontal axis as the jig is placed on or removed from the tooth. Preferably, but not necessarily, special tweezers 60 may be used, as described below, to grip the ball 51 of the handle structure 50. Use of the jig 10 to place a bracket 30 on a tooth 20 is illustrated in FIGS. 1–3 using tweezers 60 having a pair of hemispherical-shaped gripping jaws 62 on a spring metal handle 63 that is configured so that the jaws 62 are normally closed.

Referring to FIG. 1, to a jig 10 having a handle 50 of the ball or knob type, is attached an orthodontic bracket 30, which is connected to the jig body 11 by the peg 41. The bracket 30 is generally oriented on the peg 41 so that the pad or base 31 of the bracket 30 faces toward the cavity 12 of the bracket body 11. The bracket 30 is somewhat rotatable on the peg 41 so that small mis-orientation will automatically be corrected when the jig-locating surface 13 is positioned on the crown of the proper tooth. The base 31 of the bracket 30, before being placed against the tooth 20, is coated with a dental adhesive 33 of any of a number of types used to bond orthodontic appliances to teeth. Such adhesive may be of a type applied by the practitioner before placing the appliance on the tooth or may be of a type that is applied to the bracket upon manufacture or by the orthodontic appliance supply company before being provided to the orthodontic practitioner.

This combination of jig 10 and bracket 30 is picked-up by an orthodontic practitioner who grips the ball 51 with the jaws 62 of the tweezers 60 and orients the combination over the crown of the tooth 20 of the patient. Then the practitioner lowers the combination onto the tooth 20 by lightly pressing the jig-locating surface 13 against the occlusal edge of the tooth 20 and seating the cavity, which is comparable to a negative impression of a portion of the occlusal surface of the tooth 20, at a unique position and orientation on the crown of the tooth 20 with the base 31 of the bracket 30 in its correct bonding position against the facial side of the tooth 20, as illustrated in FIG. 2.

Once the jig 10 is on the tooth 20, the tacky adhesive 15 holds the jig 10 to the tooth 20. The tweezers 60 may then be removed while the adhesive on the base 31 of the bracket 30 is set. Where UV curable adhesive is used, the curing is brought about by exposure of the adhesive to ultraviolet light from a curing gun 34 applied by the practitioner. The tacky adhesive 15 holds the jig 10 and the bracket 30 in place, freeing the hands of the practitioner.

After the dental adhesive 33 has set and the bracket 30 is bonded to the tooth 20, the practitioner can engage the handle 51 of the jig 10 with the jaws 62 of the tweezers 60. Once engaged with the tweezers 60, the jig 10 can be moved occlusally away from the tooth 20, causing the tacky adhesive 15 to release from the crown of the tooth 20 and the remote end 43 of the peg 41 to slide out of the hole 32 in the bracket 30, leaving the bracket 30 bonded to the tooth 20, as illustrated in FIG. 3. Then, the practitioner can remove the jig 10 from the patient's mouth.

Figure 4:
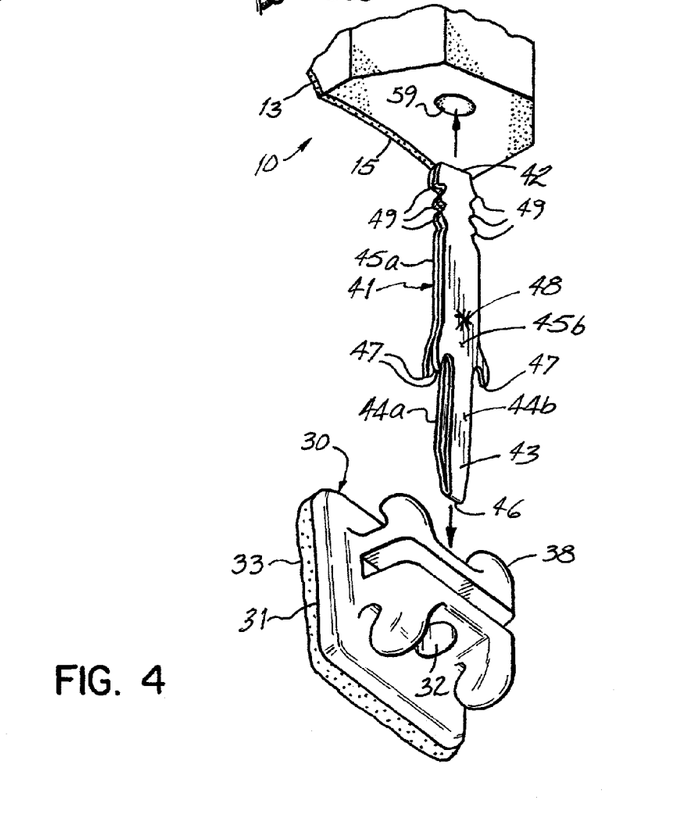
FIG. 4 is a disassembled perspective view of the assembly of the jig and bracket combination of FIG. 2.

The peg 41 of the jig 10 may be formed, as illustrated in FIG. 4, of a strip of spring sheet metal 45 (see FIGS. 5A and 5B) that has been die cut to define two matching halves 45a,45b. The strip 45 has been folded so that the halves 45a,45b form two layers joined at the juncture of the halves 45a,45b, which defines a tip 46 of the peg 41 at the remote end 43 of the peg 41.

Near the fold that defines the tip 46 of the peg 41 are smooth spring-metal sections 44a,44b of the respective halves 45a,45b. The sections 44a,44b form an outwardly expanding portion of the peg 41 that fits into hole 32 of the bracket 30. The sections 44a,44b are spring biased away from each other due to the residual stresses at the tip 46 that remain after the halves 45a,45b are folded. As such, the sections 44a,44b apply opposing normal forces on the bracket 30 at the inside surface of the hole 32 to frictionally hold the bracket 30 to the peg 41.

Outwardly extending stop wings 47, die-cut or otherwise formed in the sides of the strip halves 45a,45b, positively limit the distance that the remote end 43 of the peg 41 moves into the hole 32 of the bracket 30, to thereby precisely control the position of the bracket 30 relative to the body 11 of the jig 10. The two halves 45a,45b have a spot weld 48 joining them together in the area of the stop wings 47.

At the proximate end 42 of the peg 41, serrations 49 are formed in the edges of the two halves 45a,45b. These serrations 49 are provided to bite into the material of the jig body 11 when it is inserted into a hole 59 in the body 11 to securely hold the peg 41 in the body 11 in a more or less permanent connection, that is, a connection that will hold the peg 41 to the body 11 as the bracket 30 is inserted onto or removed from the remote end 43 of the peg 41. Once the peg 41 is fixed to the body 11 of the jig 10 with the end 42 of the peg 41 inserted into the hole in the body 11, the peg 41 is not easily removable from the body 11. On the other hand, placement of the remote end 43 of the peg 41 into the hole 32 of the bracket 30 holds the bracket 30 to the jig 10 with enough friction to prevent the bracket 30 from falling off of the peg 41 when the assembly is being moved, but with a low enough friction to allow the jig 10 to be easily removed from the bracket 30 once the bracket 30 is bonded to the tooth 20.

The peg 41 is fixed to the body 11 of the jig 10 in a precise position relative to the cavity 12 in the jig body 11. The cavity 12 uniquely locates the jig 10 on the occlusal surface on the crown of the tooth 20. The base 31 of the bracket 30 is located at a precise design position and orientation relative to the hole 32 in the archwire support 38 of the bracket 20 so that the bracket 20 will be positioned by the jig 10 at its predetermined position on the tooth 20. As a result, placement of the jig 10 on the tooth 20, with the cavity 12 uniquely positioned on the crown of the tooth 20, locates the base 31 of the bracket 30 in its exact design position on the surface of the crown of the tooth 20 for bonding to the tooth.

Figure 5A:
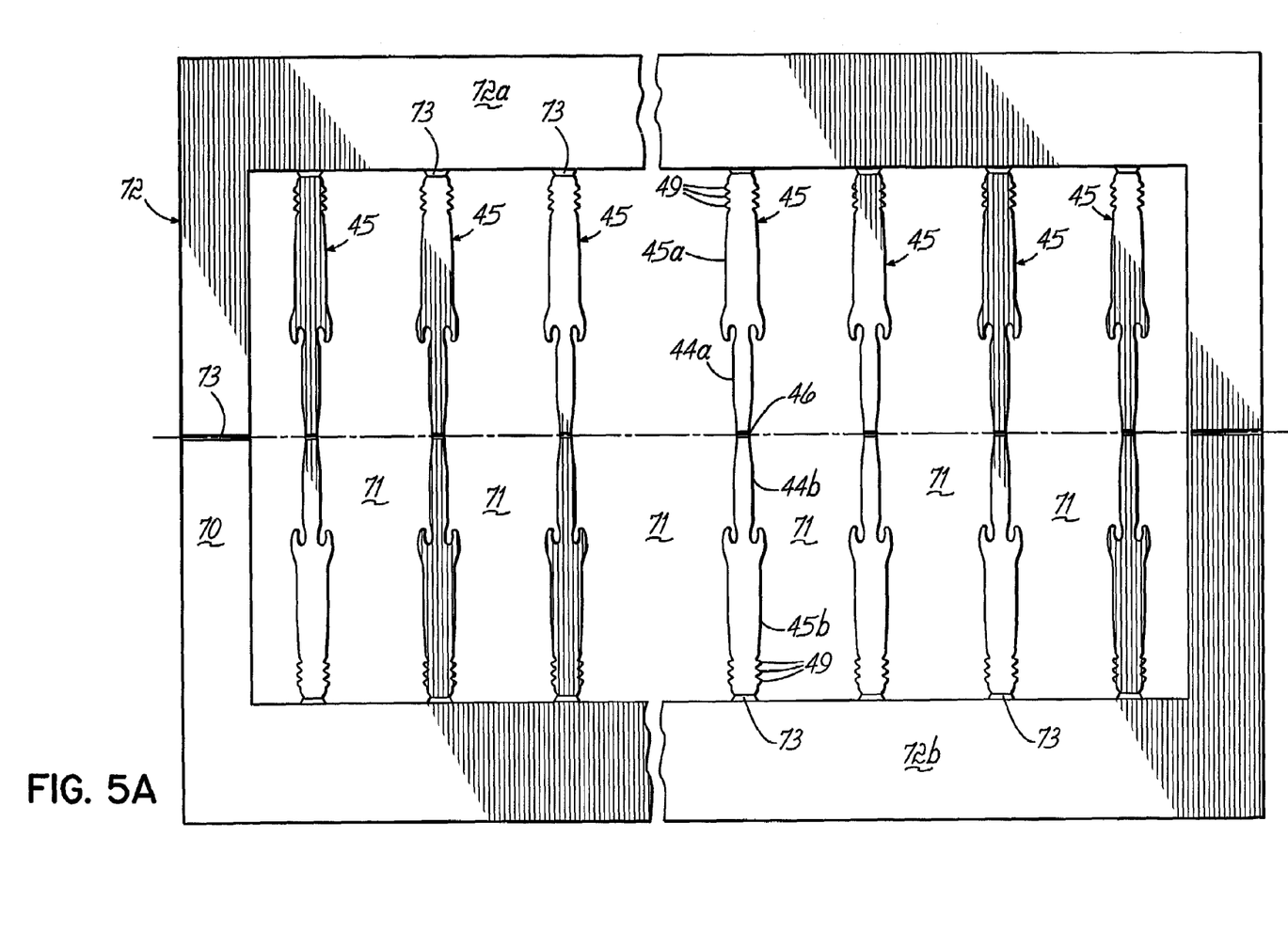
FIG. 5A is a top view of a sheet of spring metal material showing a plurality of pegs for jigs of FIG. 4 in the process of manufacture.

One method of forming the pegs 41 is to die cut a number of strips 45 from a single sheet of spring metal sheet 70, as illustrated in FIG. 5A. This may be accomplished by cutting out spaces 71 in the spring metal sheet 70, leaving the proximate ends 42 of the halves 45a,45b of the continuous strips 45 respectively connected to opposite border segments 72a,72b of a border 72 of the sheet 70. A weakness 73 is formed in the metal, for example by photo-etching, between each proximate end 42 of the strip 45 and each border segment 72a,72b to facilitate the separation of the strips 45 from the sheet 70. Another line of weaknesses 74 is formed in the sheet 70 separating the border segments 72 from each other and defining a fold line at which is formed the tips 46 of the strips 45.

Figure 5B:
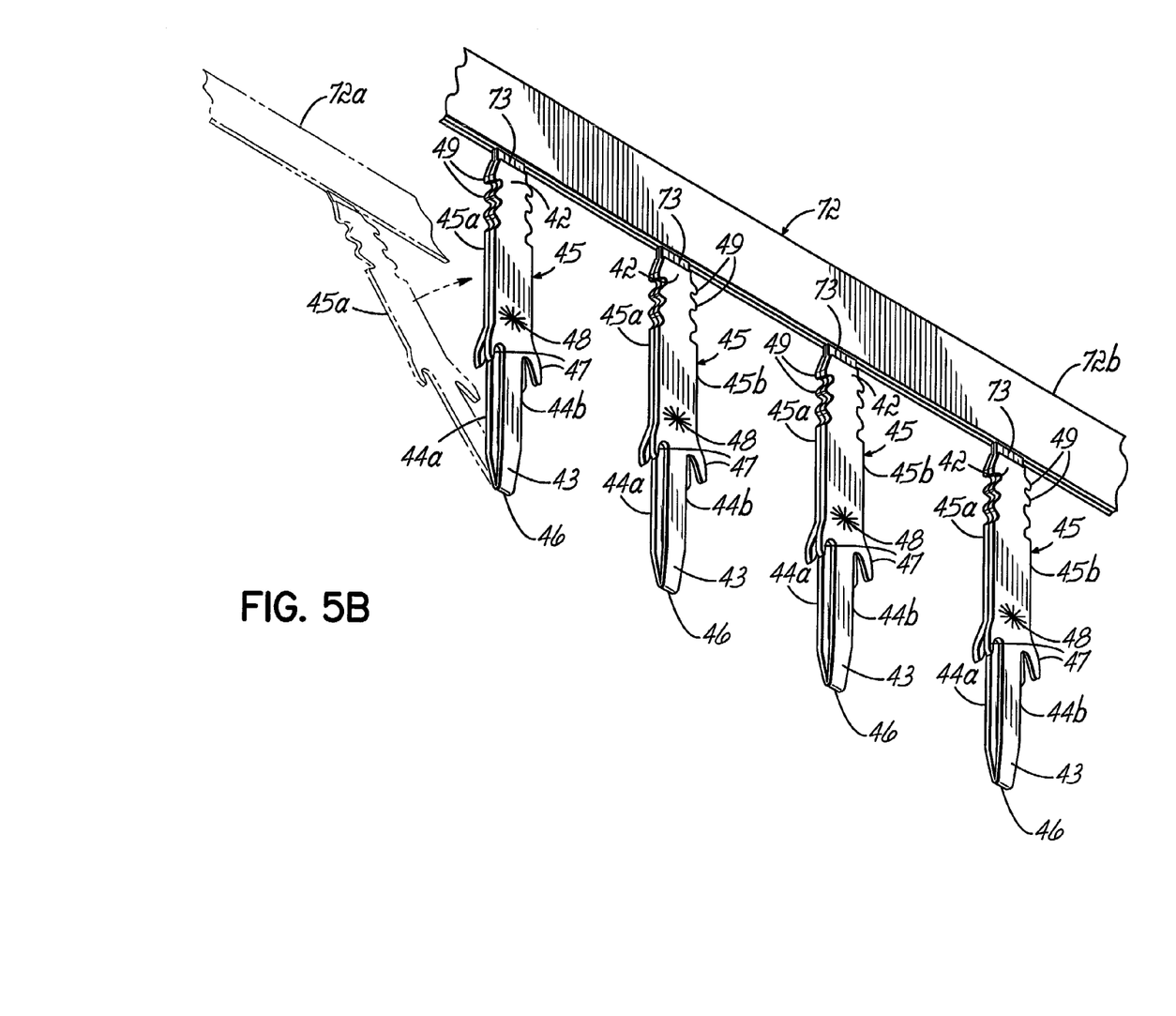
FIG. 5B is a perspective view of the sheet of material of FIG. 5A illustrating the pegs later in the process of manufacture.

The sheet 70 is folded along the line 74 to simultaneously fold each of the strips 45 along the fold at the peg tips 46, forming the two layered pegs 41, as illustrated in FIG. 5B. Once folded, the pegs 41 can be spot welded at welds 48 as shown. Then, the pegs 41 are separated from the sheet 70 by breaking them from the border segments 72a,72b at the weakness lines 73.

Figures 6A, 6B:
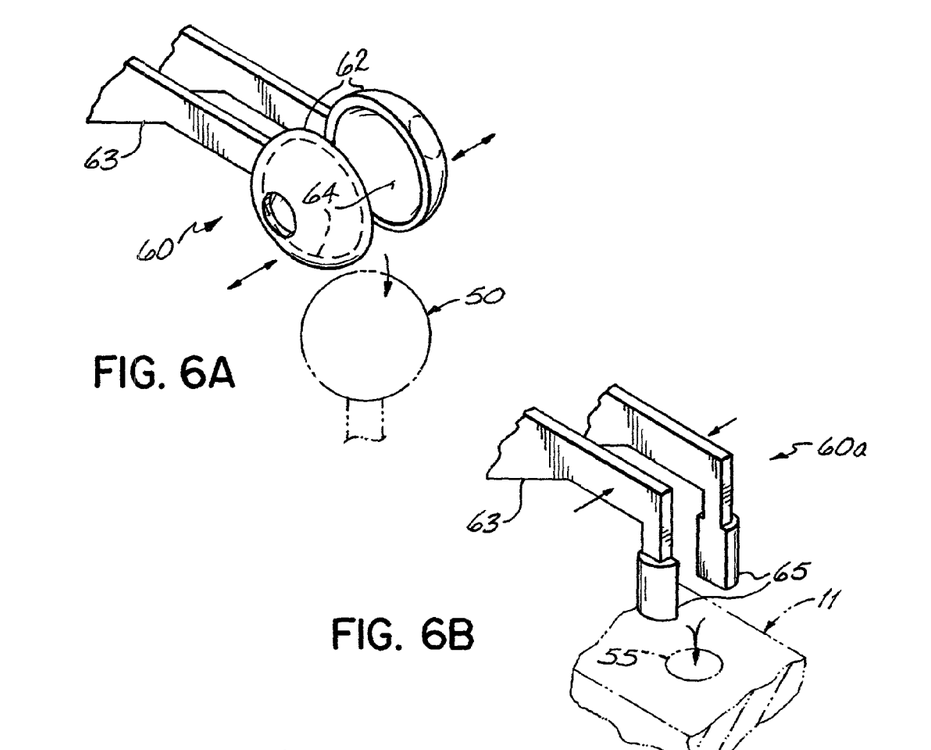
FIGS. 6A–6C are partial perspective views of alternative handle structure and gripping tool combinations for the jig of FIG. 1.
Figure 6C:
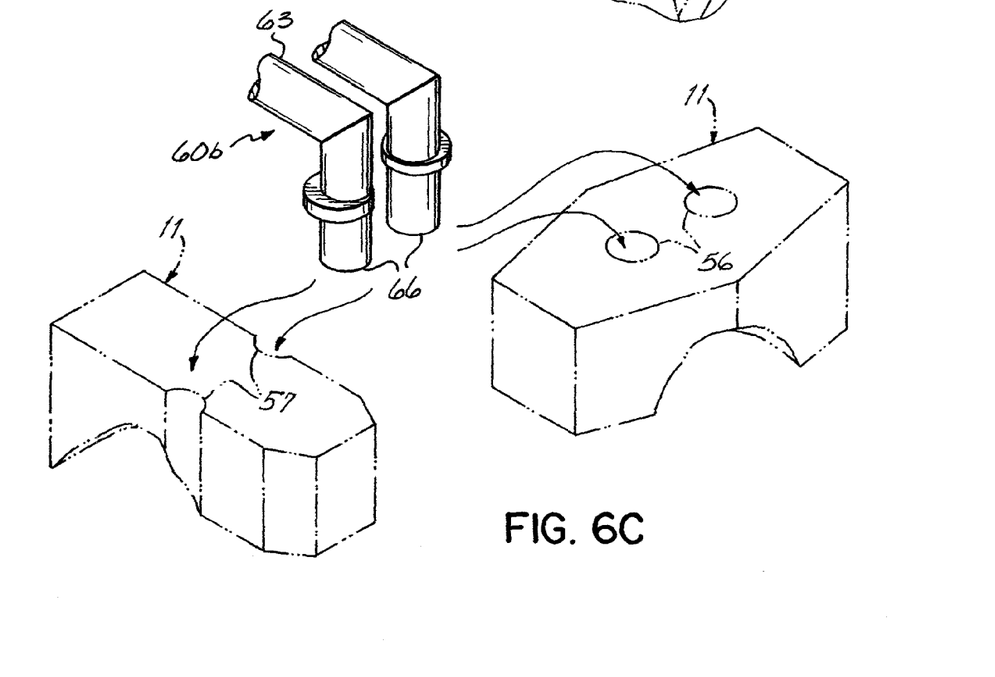

The handle structure 50 of the jigs 10 may take any of many forms. The knob 51 described above is illustrated in more detail in the embodiment of FIG. 6A, in which the jaws 60 of the tweezers 60 have concave gripping surfaces 64 that have a curvature that conforms to the outer surface of the knob 51. This configuration allows the practitioner to select the orientation of the jig 10 as held by the tweezers 50 over a wide angle. In the embodiment of FIG. 6B, the handle structure 50 in the jig body 11 is in the form of a hole 55. The jaws of tweezers 60a are semi-cylindrical spreader type jaws 65 that fit into the hole 55 and spread apart to grip the jig body 11. Preferably, the tweezers are configured so that the jaws 65 spread normally apart unless squeezed by the practitioner. Alternatively, as illustrated in FIG. 6C, the handle structure 50 in the jig body 11 may be in the form of a pair of holes 56 in the top of the jig body 11 or a pair of notches 57 in the sides of the jig body 11. The jaws of tweezers 60b may then be in the form of a pair of dowels 66 designed to grip the jig body 11 between the two dowels 66 by engaging the holes 56 or notches 57.

In most cases, the jigs 10 as illustrated in FIGS. 1–3 have cavities 12 having surfaces 13 that are adequate to accurately and uniquely position and orient the jig 10 on a tooth 20 where the width of the surface 13 of the jig spans only a portion of the width of the crown of a tooth 20. With some teeth, the crown has insufficient features on which to align the jig. For example, the occlusal tip of a cuspid 90 (FIGS. 7 and 8) has a single cusp that is relatively symmetrical around the axis of the tooth, providing a relatively spherical tip. In some patients, this crown may have a shape that permits a jig to rotate on the crown of the tooth. In such situations additional structure is desirable by which to register the jigs in their proper orientations on the teeth. Two embodiments of a jig 10 are provided having such features, as illustrated in FIGS. 7 and 8.

Figure 7:
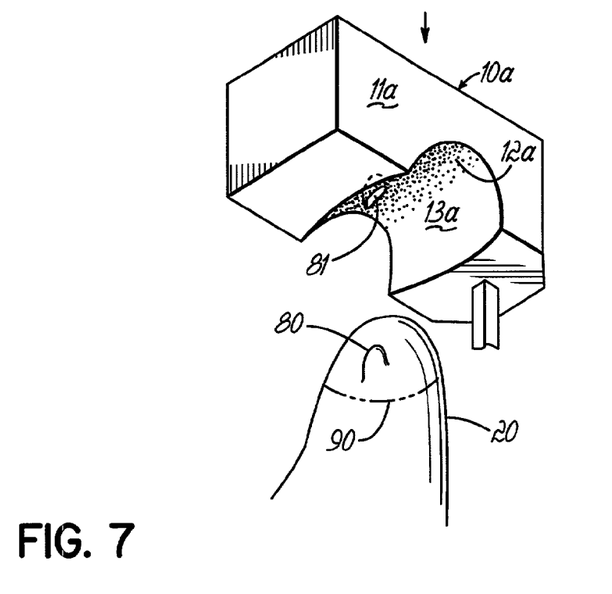
FIG. 7 is a perspective view of one embodiment of a placement jig employing registration structure to facilitate locating the jig on a tooth.

In FIG. 7, a jig 10a is shown, which is provided with a body 11a having a cavity 12a that is formed in the same manner as the cavity 12 of the jigs 10 described above. The cavity 12a has a custom three-dimensional surface 13a formed to conform to the contact portion 90 of a crown of a tooth. Prior to acquiring the three-dimensional tooth shape data for forming the cavity 12a, the surface of the tooth 20 of the patient is modified with the addition of a registerable structure 80, such as a projection or groove or other readable mark. The registerable structure 80 is shown in FIG. 7 as being a projection that is bonded to the crown of the tooth at a position where it will not interfere with the occlusion, such as on the lingual side of a lower tooth or the facial side of an upper tooth. The structure 80 is scanned with the surface of the tooth in acquiring three-dimensional tooth-shape data that is used to manufacture the cavity 12a of the jig 10a. The jig 10a is then manufactured to conform to the three-dimensional shape of the tooth crown including the structure 80, so that the tooth-conforming surface 13a of the cavity 12a has a shape 81 conforming to the tooth crown having the structure 80 thereon. The surface of the structure 80 should be parallel to the axis of the tooth or face occlusally so it is free of overhangs and surfaces that would form an interlock with a conforming jig surface 12a and thereby prevent the placement onto or removal from the tooth of the jig 10a.

Figure 8:
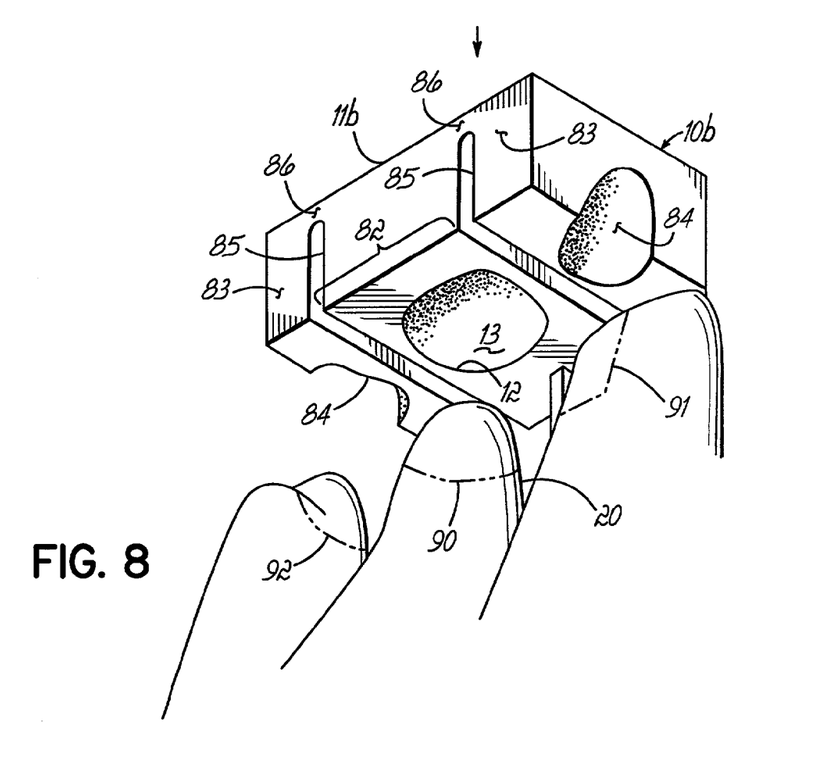
FIG. 8 is a perspective view of an alternative embodiment to that of FIG. 7 employing structure for using adjacent teeth for registering the location of the jig on a tooth.

In FIG. 8, a jig 10b is illustrated having another feature that facilitates the registration of the jig on a tooth. The jig 10b is provided with a wide body 11b having a central section 82 that has a cavity 12 formed therein, in the same manner as with the jig 10 described above, having a surface 13 that conforms to the three-dimensional shape of the crown of the tooth. Additionally, the body 11b is provided with one or two side extensions 83 configured to contact a portion 91,92 of the crown of one or both adjacent teeth. Each of the side sections 83 has a cavity or depression 84 therein having a surface that is formed to the three-dimensional shape of a portion of the crown of one of the adjacent teeth. This portion 91,92 of the crown of an adjacent tooth may be a small portion on or near the mesial or distal edge of the adjacent tooth.

The locations of the depressions 84 are located on the body 11b relative to the central cavity 12 based on three-dimensional scan data of the teeth in their pre-treatment malocclused condition. The jig 10b with the side sections 83 ceases to be able to accurately use adjacent teeth for registration as the teeth move from their initial positions, rendering them less useful for subsequent placement of an appliance that has to be rebonded later in the treatment. Such rebonding may be necessary where a bond fails or when an appliance must be removed and replaced for some other reason. To make jigs 11*b* reusable, the side sections 83 are separated from the central section 82 of the body 11*b* by a slot 85 and are connected to the central section 82 by a narrow web 86, which can be broken to remove the side sections 83 from the central section 82, thereby rendering the jig 11*b* reusable for rebonding of an appliance later in the course of treatment.

Those skilled in the art will appreciate that the application of the present invention herein is varied, that the invention is described in certain embodiments, and that additions and modifications can be made without departing from the principles of the invention. Therefore, the following is claimed:

The invention claimed is:

1. A method of providing a custom placement jig for positioning an orthodontic appliance on a tooth, the method comprising:

forming a jig body of a jig forming material, including forming a generally-concave jig-locating surface in the body in response to digitized data representing the shape of an occlusal portion of a crown of an individual tooth of an orthodontic patient;

coating the jig-locating surface with a releasable adhesive;

removably connecting an orthodontic appliance having a bonding base to the jig body;

positioning the jig body on the occlusal portion of the crown of the tooth by removably attaching the jig-locating surface thereto with the releasable adhesive and thereby generally simultaneously locating the appliance on the crown of the tooth;

adhesively bonding the located appliance to the crown of the tooth with dental adhesive between the tooth and the bonding base;

with the appliance bonded to the tooth, removing the jig body from the tooth by detaching the jig-locating surface from the crown of the tooth and disconnecting the jig body from the appliance;

providing handle structure on the jig body occlusally opposite from the jig-locating surface and configured to be gripped by a tool for transporting the combination to the tooth of the patient; and the positioning including gripping the handle structure with a tool and transporting the jig with the appliance attached to the crown of the tooth.

2. The method of claim 1 wherein:

the removing of the jig body from the tooth includes gripping the handle structure with an opposed-jaw gripper tool and therewith moving the jig body from the tooth and thereby detaching the jig-locating surface from the crown of the tooth and disconnecting the jig body from the appliance.

3. The method of claim 1 wherein:

the forming of the jig body includes forming the jig-locating surface into the jig forming material in the body in response to digitized three-dimensional data of the shape of at least a portion of a crown of an individual tooth scanned from the shape of the tooth of an orthodontic patient.

4. A method of providing a custom placement jig for positioning an orthodontic appliance on a tooth, the method comprising:

forming a jig body of a jig forming material, including forming a generally-concave jig-locating surface in the body in response to digitized data representing the shape of at least a portion of a crown of an individual tooth of an orthodontic patient;

coating the jig-locating surface with a releasable adhesive;

removably connecting an orthodontic appliance having a bonding base to the jig body;

positioning the jig body on the crown of the tooth by removably attaching the jig-locating surface thereto with the releasable adhesive and thereby generally simultaneously locating the appliance on the crown of the tooth;

adhesively bonding the located appliance to the crown of the tooth with dental adhesive between the tooth and the bonding base;

with the appliance bonded to the tooth, removing the jig body from the tooth by detaching the jig-locating surface from the crown of the tooth and disconnecting the jig body from the appliance; and the removably connecting of the orthodontic appliance to the jig body includes rigidly fastening a peg at one end thereof to the jig body releasably connecting the other end of the peg to the orthodontic appliance with less strength than the peg is fastened to the body of the jig.

5. The method of claim 4 further comprising:

cutting the peg from a single sheet of spring metal that is folded to form a plurality of outwardly biased members configured to releasably hold an orthodontic appliance to the jig when the members are inserted in a hole in the appliance.

6. The method of claim 5 wherein:

the cutting of the peg includes forming serrated edges on the opposite ends of a strip of the sheet material; and the method further includes:

folding the peg at a central portion thereof, and inserting the end of the peg having the serrated edges into the jig body to support the peg rigidly on the jig body.

7. The method of claim 6 further comprising:

welding the opposite ends together leaving a pair of outwardly biased members between the central portion and said ends that are configured to releasably hold the orthodontic appliance to the peg with less strength than the peg is held to the jig body.

8. The method of claim 4 further comprising:

the forming of the jig body includes forming the jig-locating surface into the jig forming material in the body in response to digitized three-dimensional data of the shape of at least a portion of a crown of an individual tooth scanned from the shape of the tooth of an orthodontic patient.

9. An orthodontic appliance positioning jig comprising:

a jig body having a generally-concave jig-locating surface formed therein to the negative shape of the crown of a tooth;

a coating of releasable adhesive on the jig-locating surface sufficient to removably hold the jig on the crown of the tooth;

orthodontic appliance connecting structure configured to removably support an orthodontic appliance on the body in position for bonding to the tooth when the jig-locating surface of the body is fit on the crown of the tooth; and the orthodontic appliance connecting structure includes a peg rigidly fixed at one end thereof to the body of the jig and configured at the other end thereof to releasably hold the orthodontic appliance to the peg with less strength than that by which the peg is held to the body of the jig.

10. The jig of claim 9 further comprising:
handle structure on the body remote from the jig-locating surface and positioned to balance moments that would cause tipping of the jig on the tooth when force is applied to the handle in a gingival-occlusal direction.

11. The orthodontic appliance positioning jig of claim 9 wherein:
the orthodontic appliance connecting structure includes structure on the jig body configured to removably support an orthodontic appliance on the body in position for bonding to the tooth when the jig-locating surface of the body is fit on the crown of the tooth, the connecting structure being configured to separate from the appliance to facilitate removal of the jig from the appliance.

12. A combination of an orthodontic appliance and the jig of claim 9 further comprising:
an orthodontic appliance having a bonding base configured to be bonded to the crown of the tooth, the appliance being removably connected by the connecting structure to the body of the jig and positioned relative to the jig-locating surface for locating at a bonding position on the crown of the tooth.

13. The combination of claim 12 further comprising:
a coating of uncured dental adhesive on the bonding base of the appliance.

14. The combination of claim 13 further comprising:
handle structure on the jig body remote from the jig-locating surface and configured to be gripped by a tool for transporting the combination to the tooth of the patient.

15. The combination of claim 12 wherein:
the jig body is formed of a single piece of machinable material; and
the jig-locating surface is machined into said material to conform to the custom shape of the crown of the individual tooth of the orthodontic patient.

16. The combination of claim 12 wherein the jig further comprises:
handle structure on the body remote from said jig-locating surface and configured to be gripped by a tool for transporting the jig to or from the tooth of the patient.

17. The combination of claim 16 wherein:
the jig body is formed of a single piece of machinable material;
the jig-locating surface is machined into the material to conform to the custom shape of the crown of the individual tooth of the orthodontic patient; and
the orthodontic appliance connecting structure includes a peg rigidly held at one end thereof to the body of the jig and configured at the other end thereof to releasably hold the orthodontic appliance to the peg with less strength than that which holds the peg to the body of the jig.

18. The jig of claim 9 further comprising:
handle structure on the body remote from the jig-locating surface and configured to be gripped by a tool for transporting the jig to or from the tooth of the patient.

19. The jig of claim 18 wherein:
the handle structure includes a knob projecting from the body opposite the jig-locating surface and configured to be gripped by opposed mating jaws of a gripper tool.

20. The jig of claim 18 wherein:
the handle structure includes at least one cutout in the side of the body opposite the jig-locating surface and configured to receive opposed fingers of a gripper tool.

21. A kit including the jig of claim 18 and further comprising:
a jig handling tool having opposed arms configured to grip the handle structure of the jig when squeezed by opposed fingers of a user and to otherwise normally release the jig.

22. An orthodontic appliance positioning jig comprising:
a jig body having a generally-concave jig-locating surface formed therein to the negative shape of the crown of a tooth;
a coating of releasable adhesive on the jig-locating surface sufficient to removably hold the jig on the crown of the tooth;
orthodontic appliance connecting structure configured to removably support an orthodontic appliance on the body in position for bonding to the tooth when the jig-locating surface of the body is fit on the crown of the tooth;
the jig body is formed of a single piece of machinable material;
the jig-locating surface is machined into the material to conform to the custom shape of the crown of the individual tooth of the orthodontic patient; and
the orthodontic appliance connecting structure includes a peg rigidly held at one end thereof to the body of the jig and configured at the other end thereof to releasably hold the orthodontic appliance to the peg with less strength than the peg is held to the body of the jig.

23. The jig of claim 22 wherein:
the peg is cut from a single sheet of spring metal that is folded to form a plurality of outwardly biased members configured to releasably hold an orthodontic appliance to the jig when the members are inserted in a hole in the appliance.

24. The jig of claim 22 wherein:
the peg is cut from a single sheet of spring metal and folded at a central portion with the opposite ends in proximity to form a plurality of outwardly biased members between the central portion and said ends that are configured to releasably hold an orthodontic appliance to the jig when the folded central portion is inserted in a hole in the appliance; and
the ends being effective to hold the peg to the body when said ends are inserted into the body with greater strength than the members releasably hold the appliance to the peg.

25. The jig of claim 22 wherein:
the peg is cut from a single sheet of spring metal shaped to form a plurality of outwardly biased members configured to releasably hold an orthodontic appliance to the jig when inserted into a hole in the appliance; and
the peg having an end effective, when inserted into the body, to hold the peg to the body with greater strength than the members releasably hold the appliance to the peg.

26. An orthodontic appliance positioning jig comprising:
a jig body having a generally-concave jig-locating surface formed therein to the negative shape of an occlusal portion of the crown of a tooth;
handle structure on the body occlusally opposite from the jig-locating surface and configured to be gripped by a tool for transporting the jig to or from said tooth, the handle structure being positioned to balance moments that would cause tipping of the jig on the tooth when force is applied to the handle in a gingival-occlusal direction; and orthodontic appliance connecting structure on the body configured to removably support an orthodontic appliance on the body in position for bonding to the tooth when the jig-locating surface of the body is fit on the crown of the tooth.

27. The jig of claim 26 wherein:

the orthodontic appliance connecting structure includes a peg rigidly fixed at one end thereof to the body of the jig and configured at the other end thereof to releasably hold the orthodontic appliance to the peg with less strength than that by which the peg is held to the body of the jig.

28. The jig of claim 26 wherein:

the handle structure includes a knob projecting from the body opposite the jig-locating surface and configured to be gripped by opposed mating jaws of a gripper tool.

29. The jig of claim 26 wherein:

the hand structure includes at least one control cutout in the side of the body opposite the jig-locating surface and configured to receive opposed fingers of a gripper tool.

30. A kit including the jig of claim 26 and further comprising:

a jig handling tool having opposed arms configured to grip the handle structure of the jig when squeezed by opposed fingers of a user and to otherwise normally release the jig.

31. A method of making a placement jig for positioning an orthodontic appliance on a tooth, the method comprising:

cutting a spring metal sheet to form two border segments and at least one strip of metal extending between said two border segments, the strip having an end portion attached to a respective one of the border segments and a pin portion between the end portion and the other border segment;

forming the pin portions into a plurality of surface resiliently biased away from each other;

separating the strips from the border sections to form a peg of the separated strip; and securely attaching the peg to a jig body by inserting the end portion of the peg into the jig body.

32. The method of claim 31 wherein:

the strip has two halves, each of the halves having an end portion attached to a respective one of the border segments and a pin portion extending between the end portion of the respective half and the pin portion of the other half;

the forming includes folding the cut sheet such that the strip folds at the junction of the pin portions of the two halves of the strip so that the halves lie parallel to and in proximity with each other and are resiliently biased away from each other;

the separating includes separating the strip at the end portions from the border sections to form a peg of the separated strip; and the attaching includes securely attaching the peg to a jig body by inserting the end portions of the peg into the jig body.

33. The method of claim 32 further comprising:

welding the end portions of the halves together.

34. The method of claim 33 wherein:

the cutting includes cutting an opening in the sheet with border portions extending therearound and cutting a plurality of the strips of metal extending across the opening, the cutting further including the forming of a weakness across each of the strips in a common alignment with each other so that the sheet, when folded along a line containing the weaknesses, folds the halves of each of the strips.

35. The method of claim 31 further comprising:

removably connecting an orthodontic appliance having a bonding base to a jig body by inserting the pin portion thereof into a hole in the appliance.

36. The method of claim 31 wherein:

the cutting includes forming a weakness across the strip between the pin portions of the halves.

37. The method of claim 31 wherein:

the cutting includes cutting serrated side edges on the end portions and relatively smooth edges on the pin portions.

38. An orthodontic appliance placement jig made according to the method of claim 31.

39. The method of claim 31 further comprising:

forming a jig positioning cavity on the jig body and providing a handle on the jig body, on an opposite side thereof from the cavity.

40. The method of claim 39 further comprising:

providing a jig handling tool having jaws configured to grip the handle to position and remove the jig from a tooth.

41. The method of claim 31 further comprising:

providing an orthodontic appliance having a hole configured to receive the peg to hold the appliance and jig together, the hole being positioned on the appliance and the peg being positioned on the jig body so as to locate the appliance at a design position on a tooth when the jig is fitted to the tooth.

42. The jig of claim 26 wherein:

The jig body has a generally-concave jig-locating surface having the shape of the crown of a tooth;

said surface being coated at least in part with a releasable adhesive.

43. The jig of claim 42 further comprising:

an orthodontic appliance connector configured to removeably connected an orthodontic appliance to the jig body in a predetermined relationship to the jig locating surface.

44. A jig and orthodontic appliance assembly including the jig of claim 43 and further comprising:

an orthodontic appliance having a bonding base removeably connected to the jig body by the connector.

45. A method of proving a jig for positioning an orthodontic appliance on a tooth comprising:

forming a jig body having a central section having a generally-concave jig-locating surface formed therein that is configured to fit onto the crown of a tooth;

providing registration structure beyond the natural features of the particular tooth that is adapted to orient the jig on the tooth;

the registration structure being provided by forming one or more removable extensions on the jig body configured to register with one or more immediately adjacent teeth, the registration structure having a generally-concave jig-locating surface formed in the extension that is configured to fit against the crown of an immediately adjacent tooth when the particular tooth and the immediately adjacent tooth are in initial malocclused condition; and each extension including a side section of the body, and the body having a slot therein between the central section and each side section thereof forming a breakable web in the body joining the central section and respective side section, thereby making the extension removable from the central section of the body and rendering the jig reusable after the teeth have been moved.

46. A custom orthodontic appliance assembly comprising:
a custom orthodontic appliance having a bonding base configured to be bonded at a design position to the crown of a specific tooth of an individual patient;
a custom placement jig having a jig body with a generally-concave jig-locating surface formed therein to a negative shape of the crown of the specific tooth of the individual patient so as to fit at a unique position and orientation on the crown of the tooth; and
orthodontic appliance connecting structure removably supporting the orthodontic appliance on the body of the jig in position for bonding to the tooth at the design position when the jig-locating surface of the body is fit in the unique position and orientation on the crown of the tooth, the orthodontic appliance connecting structure including a peg connected at one end thereof to the body of the jig and connected at the other end thereof to the orthodontic appliance so the peg holds the appliance thereto with less strength than that by which the peg is connected to the body of the jig and with less strength than the appliance is to be bonded to the tooth.

47. The assembly of claim 46 wherein a) the bonding base is configured to be bonded at a design position to the crown of a specific tooth of an individual patient, b) the generally-concave jig-locating surface is configured with the negative shape of the crown of the specific tooth of the individual patient so as to fit at a unique position and orientation on the crown of the tooth, and c) the connecting structure is configured to support the orthodontic appliance on the body in position for bonding to the tooth at the design position, in accordance with a method comprising:

forming the generally-concave jig-locating surface in the body of the jig in response to digitized three-dimensional data representing the shape of at least a portion of a crown of the specific tooth of the individual patient.

48. The assembly of claim 47 further comprising:
a coating of releasable adhesive on the jig-locating surface sufficient to removably hold the jig on the crown of the tooth with less strength than that with which the appliance is to be bonded to the tooth.

49. The assembly of claim 46 further comprising:
a coating of releasable adhesive on the jig-locating surface sufficient to removably hold the jig on the crown of the tooth with less strength than that with which the appliance is to be bonded to the tooth.

* * * * *

UNITED STATES PATENT AND TRADEMARK OFFICE
CERTIFICATE OF CORRECTION

PATENT NO. : 7,094,053 B2  
APPLICATION NO. : 10/156162  
DATED : August 22, 2006  
INVENTOR(S) : Craig A. Andreiko It is certified that error appears in the above-identified patent and that said Letters Patent is hereby corrected as shown below:

Column 5, line 26, reads "such as a LJV curable adhesive" and should read --such as a UV curable adhesive--.

Column 15, line 39, CLAIM 31, reads "into a plurality of surface resiliently biased" and should read --into a plurality of surfaces resiliently biased--.

Column 15, line 64, CLAIM 34, reads "The method of claim 33 wherein" and should read --The method of claim 32 wherein--.

Column 16, line 35, CLAIM 42, reads "The jig body has a" and should read --the jig body has a --.

Signed and Sealed this

Tenth Day of April, 2007

JON W. DUDAS  
*Director of the United States Patent and Trademark Office*